(12) United States Patent
Skinner et al.

(10) Patent No.: US 7,060,218 B2
(45) Date of Patent: Jun. 13, 2006

(54) ADJUSTABLE LENGTH MOLD ASSEMBLIES

(75) Inventors: Johann J. Skinner, Cupertino, CA (US); Kerry J. Williams, Temecula, CA (US); Jonathan P. Durcan, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 10/990,046

(22) Filed: Nov. 16, 2004

(65) Prior Publication Data

US 2005/0087913 A1    Apr. 28, 2005

Related U.S. Application Data

(62) Division of application No. 09/801,073, filed on Mar. 6, 2001, now Pat. No. 6,835,059.

(51) Int. Cl.
*B29C 49/48* (2006.01)
*B29D 23/00* (2006.01)

(52) U.S. Cl. .................... 264/523; 264/219
(58) Field of Classification Search ............ 264/219, 264/523
See application file for complete search history.

(56) References Cited

U.S. PATENT DOCUMENTS

| | | |
|---|---|---|
| 3,837,347 A | 9/1974 | Tower |
| 3,882,852 A | 5/1975 | Sinnreich |
| 4,481,323 A | 11/1984 | Sterling |
| 4,499,045 A | 2/1985 | Obsomer |
| 4,815,960 A | 3/1989 | Rudolph |
| 4,820,349 A | 4/1989 | Saab |
| RE33,561 E | 3/1991 | Levy |
| 5,156,612 A * | 10/1992 | Pinchuk et al. ............ 606/194 |
| 5,163,989 A * | 11/1992 | Campbell et al. ............ 65/110 |
| 5,195,970 A | 3/1993 | Gahara |
| 5,223,205 A | 6/1993 | Jackowski et al. |
| 5,254,091 A | 10/1993 | Aliahmad et al. |
| 5,304,340 A | 4/1994 | Downey |
| 5,334,146 A | 8/1994 | Ozasa |
| 5,334,201 A | 8/1994 | Cowan |
| 5,338,298 A | 8/1994 | McIntyre |
| 5,358,486 A | 10/1994 | Saab |
| 5,409,495 A | 4/1995 | Osborn |
| 5,653,691 A | 8/1997 | Rupp et al. |

(Continued)

*Primary Examiner*—Robert B. Davis
(74) *Attorney, Agent, or Firm*—Fulwider Patton LLP

(57) ABSTRACT

The invention is directed to adjustable length mold assemblies for forming inflatable members and methods for using adjustable length mold assemblies for forming inflatable members, such as, for example, balloons for use with balloon catheters and stent delivery systems. The adjustable length mold assemblies comprise at least two mold pieces adapted to fit together, one mold piece having a surface configured to be slidably received by a bore of the other mold piece, the placement of one piece within the other defining a chamber of variable length which forms the mold. Each adjustable length mold assembly of the present invention is effective to form balloons, where if desired different balloons formed by a single mold may have different lengths. The adjustable length mold assemblies may also comprise a positioner to put a mold piece in a desired position relative to the other, and a locking mechanism to secure a mold piece in a desired position.

8 Claims, 11 Drawing Sheets

U.S. PATENT DOCUMENTS

| | | |
|---|---|---|
| 5,755,708 A | 5/1998 | Segal |
| 5,807,520 A | 9/1998 | Wang et al. |
| 5,810,871 A | 9/1998 | Tuckey et al. |
| 5,836,965 A | 11/1998 | Jendersee et al. |
| 5,843,116 A | 12/1998 | Crocker et al. |
| 5,871,468 A | 2/1999 | Kramer et al. |
| 5,948,345 A | 9/1999 | Patel et al. |
| 6,176,698 B1 | 1/2001 | Grantz et al. |
| 6,283,743 B1 | 9/2001 | Traxler et al. |
| 6,360,577 B1 | 3/2002 | Austin |
| 6,402,778 B1 | 6/2002 | Wang |
| 6,561,788 B1 | 5/2003 | Gaudoin |
| 6,592,550 B1 | 7/2003 | Boatman et al. |
| 2004/0147952 A1 | 7/2004 | Murray, III |

\* cited by examiner

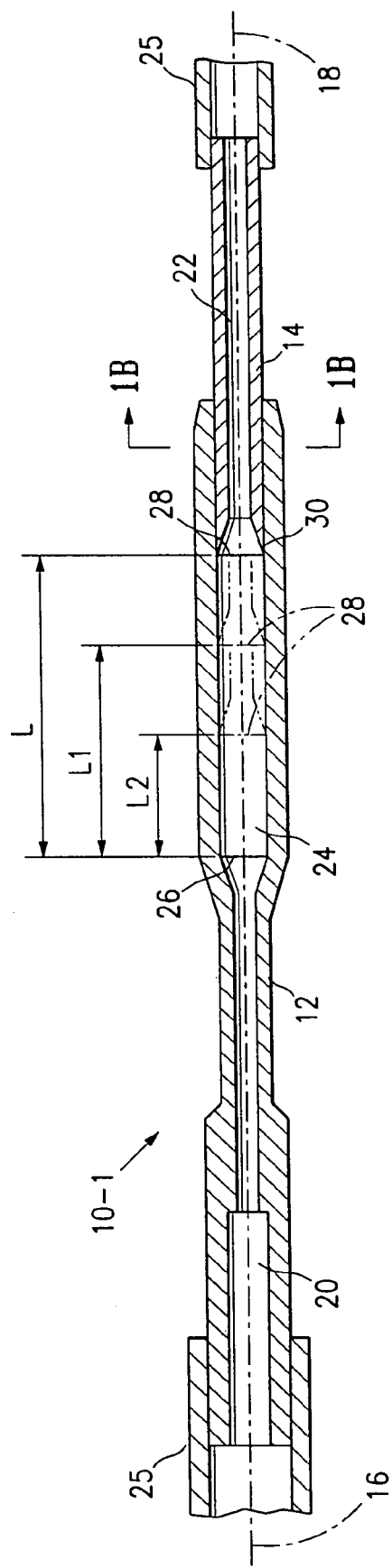
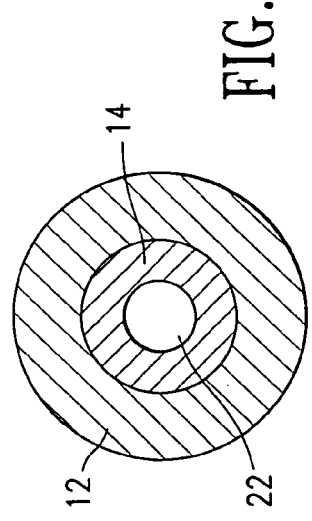
FIG. 1A
FIG. 1B

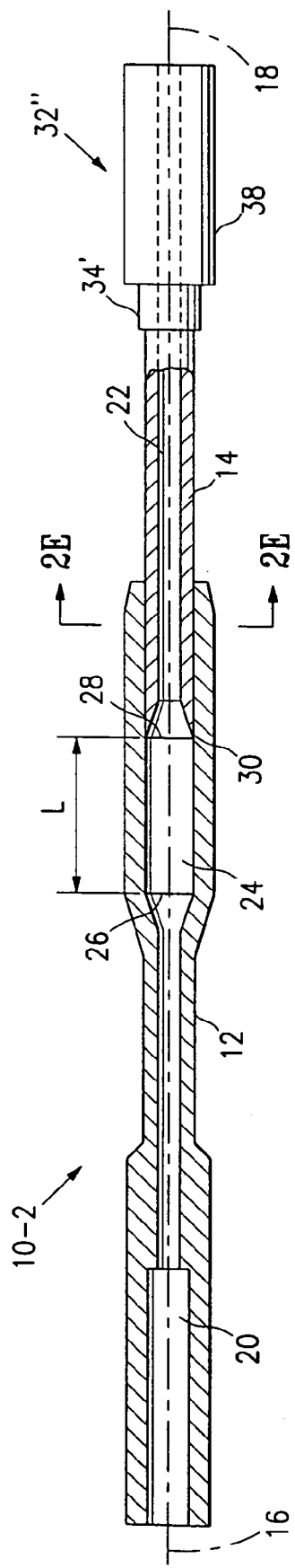
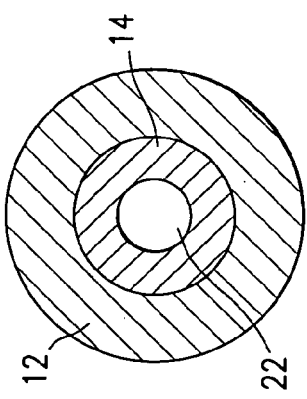
FIG. 2C
FIG. 2E

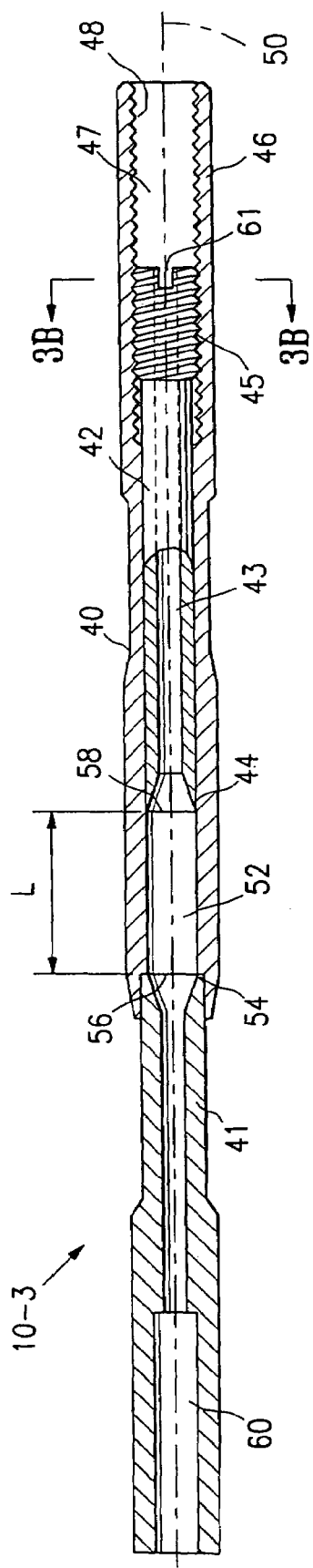
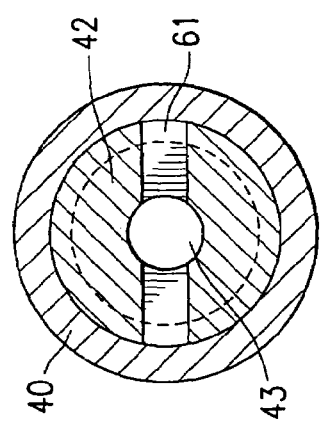
FIG. 3A
FIG. 3B

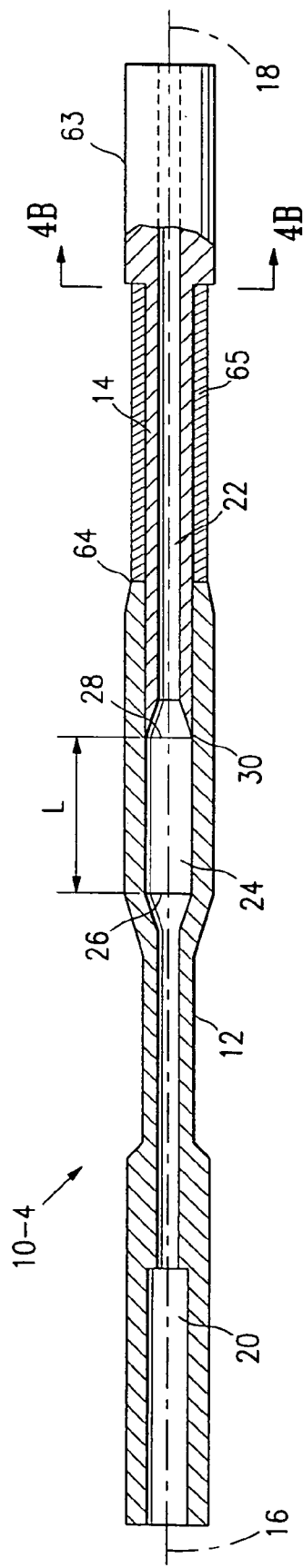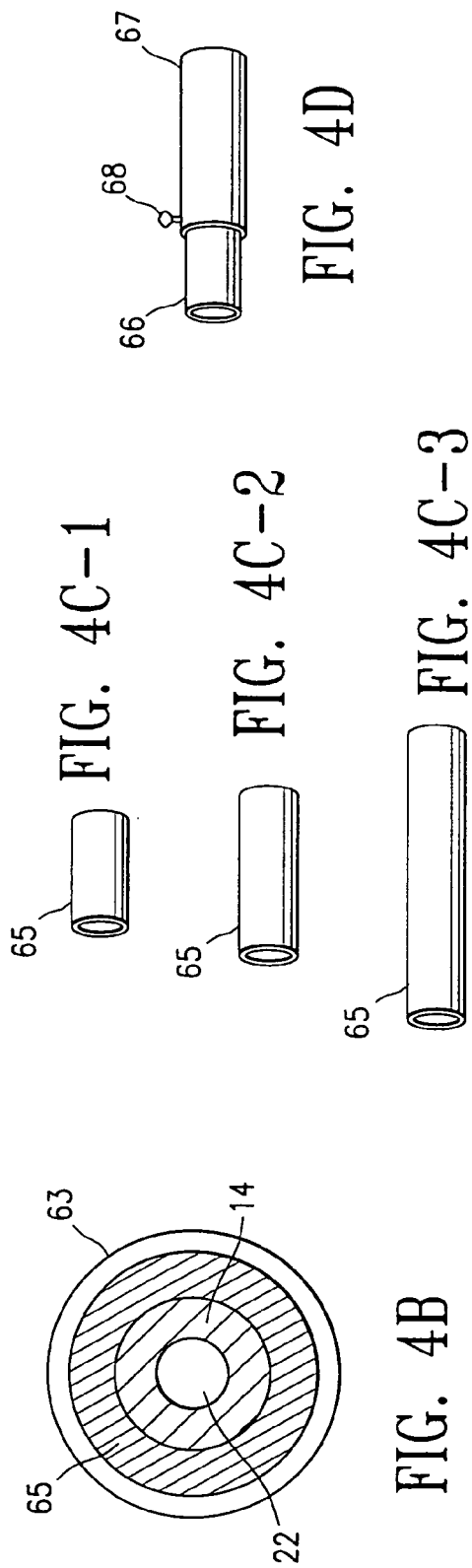
FIG. 4A
FIG. 4B
FIG. 4C-1
FIG. 4C-2
FIG. 4C-3
FIG. 4D

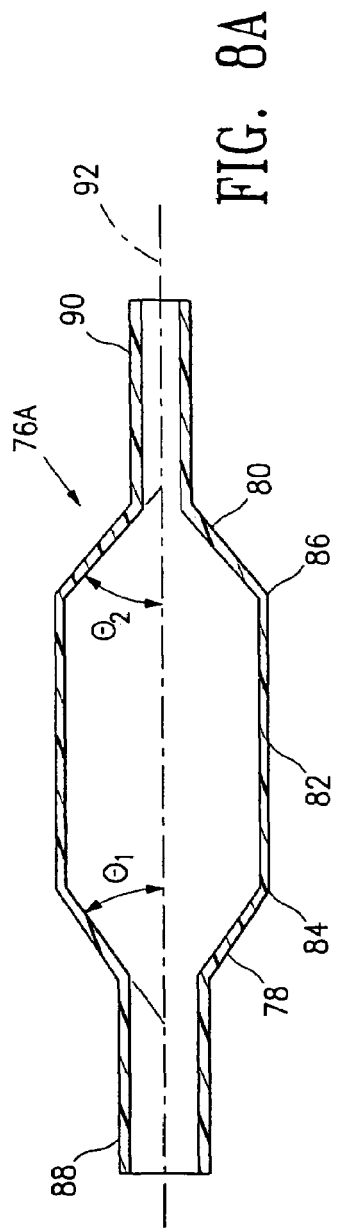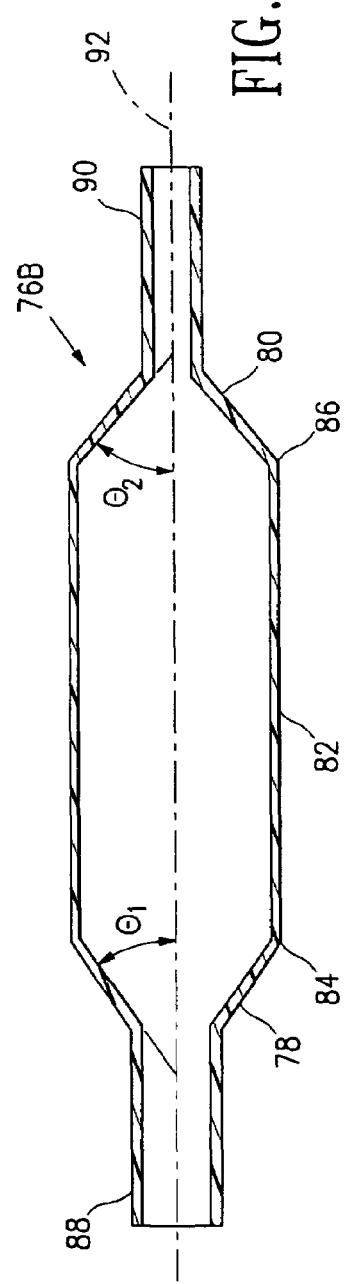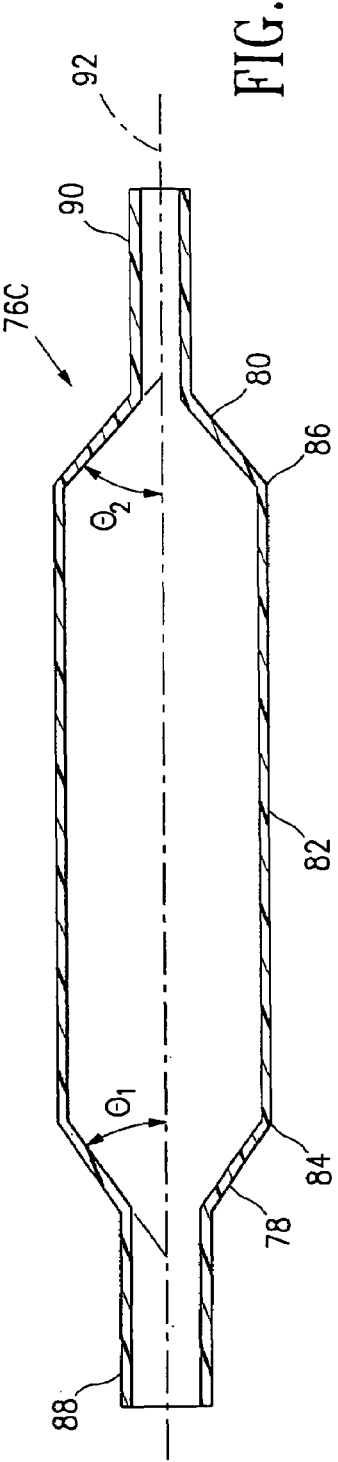

ADJUSTABLE LENGTH MOLD ASSEMBLIES

This application is a Division of Ser. No. 09/801,073, filed Mar. 6, 2001, now U.S. Pat. No. 6,835,059.

FIELD OF INVENTION

The invention relates to the field of intravascular delivery systems, and more particularly to molds for forming balloons.

BACKGROUND OF THE INVENTION

In percutaneous transluminal coronary angioplasty (PTCA) procedures to treat a stenosis in an artery, a guiding catheter is advanced until the distal tip of the guiding catheter is seated in the ostium of a body lumen, such as a coronary artery. A guide wire, positioned within an inner lumen of a dilatation catheter, is first advanced out of the distal end of the guiding catheter into the patient's coronary artery until the distal end of the guide wire crosses a lesion to be dilated. Then the dilatation catheter having an inflatable balloon on the distal portion thereof is advanced into the patient's cardiovascular system, over the previously introduced guide wire, until the balloon of the dilatation catheter is properly positioned across the lesion. Once properly positioned, the dilatation balloon is inflated with liquid one or more times to a predetermined size at relatively high pressures (e.g. greater than 6 atmospheres) so that the stenosis in a blood vessel is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Finally, the balloon is deflated, blood flow resumes through the dilated artery, and the dilatation catheter can be removed therefrom.

After angioplasty procedures, restenosis may form in the artery at the original stenotic site, necessitating either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion.

In the design of catheter balloons, the balloon shape and length must be tailored to provide optimal performance for a particular application, whether it be angioplasty, stent delivery, or other application. In many cases, it may be desired to produce balloons of different lengths but with similar diameters and tapers. Balloons adapted to a particular purpose may be produced in several lengths to accommodate different patient characteristics and physician preferences.

The manufacture of catheter balloons is a delicate and expensive undertaking. Typically, molds of the desired shape and size are created for each balloon design to be manufactured. Such molds are difficult and expensive to produce. In addition, each time it is desired to manufacture a different balloon catheter, time and labor must be expended in changing molds. Accordingly, there is need in the art for catheter balloon molds adaptable for use in the manufacture of multiple balloon designs so as to reduce the cost and improve the efficiency of processes for the manufacturing of inflatable members, such as balloon catheters.

SUMMARY OF THE INVENTION

The invention is directed to adjustable length mold assemblies for forming inflatable members for medical devices and methods for using adjustable length mold assemblies for forming inflatable members, such as, for example, balloons for use with balloon catheters and stent delivery systems. In a particular aspect, the invention is directed to mold assemblies for forming such balloons, each mold assembly being effective to form a variety of balloons of a variety of lengths. In another aspect, the invention comprises adjustable length mold assemblies with first mold pieces configured to form working lengths of balloon portions of inflatable members and second mold pieces configured to form tapered end sections of balloon portions of inflatable members.

The adjustable length mold assemblies of the invention for forming inflatable members for medical devices comprise a first mold piece having a first internal chamber defined at least in part by a first internal molding surface configured to form a first exterior surface of a first section of an inflatable member formed in the mold, and a second mold piece having a second internal chamber defined at least in part by a second internal molding surface configured to form a second exterior surface of a second section of the inflatable member formed in the mold, at least a portion of an outer surface of said second mold piece being configured to be slidably received by at least a portion of the first internal chamber of the first mold piece. The second mold piece may be moved so that at least a portion of the second mold piece may assume any one of a plurality of positions within the first mold piece. Inserting a portion of the second mold piece into the first mold piece complements and completes the first internal molding surface to form a variable-length chamber for molding inflatable members for medical devices.

A molding surface that complements and completes another molding surface is one that, together with the other molding surface, forms a complete molding surface having no gaps or discontinuities large enough to prevent the formation of inflatable members for medical devices.

An internal molding surface is an interior face of a bore in a mold. An exterior surface of a section of an inflatable member is the outside surface of an inflatable member, such as a balloon. A surface that is configured to correspond to an exterior surface of a section of an inflatable member is a surface that is the size and shape of a balloon that is to be formed by the mold. Thus, an internal molding surface configured to correspond to an exterior surface of a section of an inflatable member formed in a mold comprises the interior face of a bore in a mold that is the size and shape of the outside surface of a balloon that is to be formed by the mold.

For example, the working surface is an exterior surface of an inflatable member which comprises the longitudinal wall of the balloon portion of an inflatable member for a medical device, and is typically cylindrical in shape. The tapered end section is another exterior surface of an inflatable member, comprising a wall connecting the tube portion with the working surface of a balloon, the wall making an angle with respect to the tube portion of the balloon. A tapered end section typically has the shape of a section of a cone, the wall typically not being perpendicular to the tube. In addition, the tapered end section may comprise multiple portions formed at different angles to the axis of the tube.

It will be understood that, for example, the second mold piece, comprising a movable piece configured to be slidably received by the internal chamber of first mold piece may be a constituent of a group of pieces such as a second mold group, and is not restricted to a unitary second mold piece. Thus, embodiments of the invention may also include a second mold group comprising a support or extension configured to engage and hold a second mold piece having an exterior surface configured to be slidably received by the internal chamber of the first mold piece.

The diameter and shape of the variable-length chamber is defined by the size and shape of the bores of the mold pieces. The length of the variable-length chamber is defined by the length of second mold piece inserted into the first mold piece, and so may be varied over a plurality of lengths. The length of the variable-length chamber determines the length of the balloon of the inflatable member produced in the mold assembly. It will thus be understood by one of ordinary skill in the art that one adjustable length mold assembly may be used to form balloons of a variety of lengths, by adjustment of the length of the variable-length chamber through adjusting the distance that one mold piece is inserted into another mold piece.

The adjustable length mold assemblies of the present invention may further include a positioner effective to place an inner piece in a desired location within the bore of an outer piece.

The molds of the present invention may also have a locking mechanism to secure and retain the mold pieces in a desired position, effective to maintain the mold pieces and the chamber defined by them in position. Locking mechanisms may comprise, for example, a device selected from the group consisting of a screw, a sleeve, a stop, a brake, a gear, a pin, and a clamp.

The cross-sectional shape of the molds of the invention may be substantially circular, or elliptical, or lobed, or any other desired shape. A "substantially circular" shape is one that is circular to within normal variations encountered in manufacture of a mold. Where the cross-sectional shape is elliptical, the lengths of different radii may of course vary at different angular orientations around a longitudinal axis of the mold. Similarly, where the mold is lobed, lobes need not be identical, but may vary in size, shape, and other characteristics. In addition, an end of a mold piece may be flat, curved or rounded, and may make an angle or comprise surfaces making different angles with respect to the longitudinal axis of the bore of the piece, effective to form a mold chamber shaped to produce desired taper sections in balloons formed within the mold.

It will be understood that the chambers formed by the adjustable length mold assemblies of the invention provide wall surfaces effective to shape and form balloons of desired shapes and sizes when parisons of suitable composition are placed therein and heated, subjected to tension, filled with pressurized gas, and or subjected to other treatments effective to aid in the formation of balloons. Adjustable length mold assemblies of the invention are suitable for formation of balloons comprising desired shaft sizes and lengths, taper shapes and sizes, and working sections of desired length, diameter, and wall thickness.

The mold pieces of the invention may further be configured to operably connect to detachable extension shafts to connect the mold pieces to a blow-molding machine. Any suitable connection is effective to operably connect the extension shafts. Such suitable connections include pressure fittings such as luer-lock fittings, clamps, o-ring fittings, and the like and mechanical fittings such as threaded couplings, screw fittings, and snap fittings. The molds of the invention may be formed of any suitable material. In particular, the molds may comprise a metal, preferably stainless steel, for ease of fabrication, to achieve good surface quality and temperature and corrosion resiliency.

The present invention further provides a method of forming a variable length mold is provided, comprising providing an outer mold part, an inner mold part, and inserting the inner mold part at least partially within the outer mold part. Further, the invention provides a method for forming an inflatable member, the method comprising providing an adjustable length mold assembly of the invention, positioning an inner piece of the mold within the bore of an outer part, placing a parison of heat-sensitive material within the chamber, connecting the parison to a source of pressure, heating the parison, effective to soften the parison, providing pressure to the parison, effective to raise the pressure within the parison, whereby the heat-sensitive material is deformed and contacts the chamber, effective to form an inflatable member.

Use of the adjustable length mold assemblies of the invention makes it possible to rapidly, simply, and economically shift production from one balloon design to another, provides the ability to simply and quickly modify the balloon design that is produced by a mold, and readily allows for the production, by a single mold, of a variety of similar balloons that vary only in the length of one particular section, such as the length of the working section. The manufacture of inflatable members with a variety of working lengths, for example, while other parameters are the same, allows for balloons to be manufactured to more exacting working length specifications, provides more reproducible angle and diameter measurements, and affords lesser lot variability than other methods. Thus, the invention provides the advantages of greater flexibility in the manufacture of inflatable members, and of the ability to rapidly and economically alter the design of balloon members produced by a mold.

BRIEF DESCRIPTION OF THE DRAWINGS

FIG. 1A illustrates a longitudinal cross-section of an adjustable length mold assembly which embodies features of the invention, the mold assembly having two segments.

FIG. 1B is a cross-sectional view of the adjustable length mold assembly of FIG. 1A taken along line 1B—1B.

FIG. 2C illustrates a partial longitudinal cross-sectional view of an adjustable length mold assembly embodying features of the invention having mechanical positioner that is a hydraulic positioner.

FIG. 2E is a transverse cross-sectional view of an adjustable length mold assembly having a mechanical positioner embodying features of the invention, taken along line 2E—2E of FIGS. 2A, 2B, and 2C.

FIG. 3A illustrates a longitudinal cross section of an adjustable length mold assembly embodying features of the invention, the mold assembly having a threaded screw positioner.

FIG. 3B is a transverse cross-sectional view of the adjustable length mold assembly of FIG. 3A taken along line 3B—3B.

FIG. 4A illustrates a partial longitudinal-cross-section of an adjustable length mold assembly embodying features of the invention, the mold assembly having a sleeve positioner.

FIG. 4B is a transverse cross-sectional view of the adjustable length mold assembly of FIG. 4A taken along line 4B—4B.

FIG. 4C illustrates examples of three sleeves of different lengths.

FIG. 4D shows an example of an adjustable sleeve.

FIG. 8 illustrates balloon portions of inflatable members made by adjustable length mold assemblies embodying features of the invention. FIG. 8A is a longitudinal cross sectional view of a balloon showing the unwrapped balloon in the inflated condition. FIG. 8B is a longitudinal cross sectional view of a balloon of another length formed by an adjustable length mold assembly embodying features of the invention showing the unwrapped balloon in the inflated condition. FIG. 8C is a longitudinal cross sectional view of a balloon of a third length formed by an adjustable length mold assembly of the invention embodying features of the invention showing the unwrapped balloon in the inflated condition.

DETAILED DESCRIPTION OF THE INVENTION

Figure 2A:
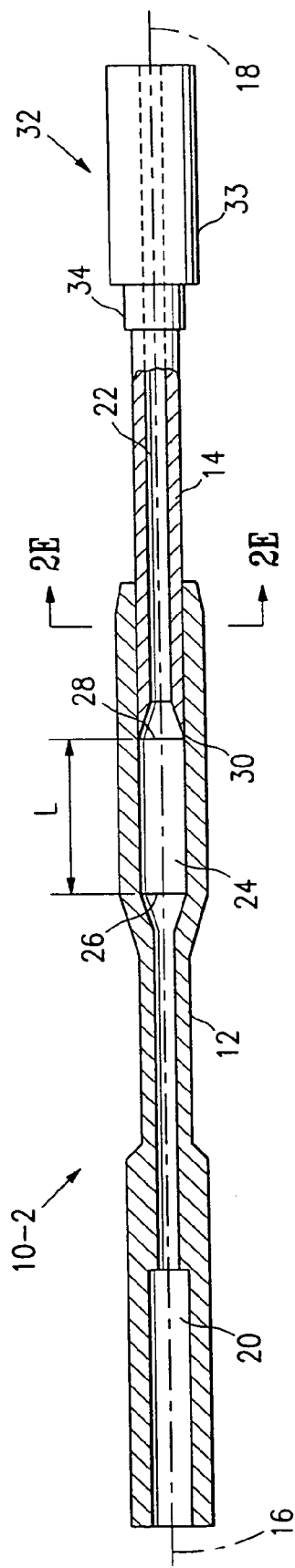
FIG. 2A illustrates a partial longitudinal cross-sectional view of an adjustable length mold assembly embodying features of the invention having mechanical positioner that is a solenoid.

FIG. 1 illustrates an adjustable length mold assembly 10-1 embodying features of the invention, and generally including a first mold piece 12, comprising an outer mold piece, and second mold piece 14, comprising an inner mold piece. The mold pieces 12 and 14 are illustrated assembled together in FIG. 1A, showing second mold piece 14 in part slidably disposed within a portion of first mold piece 12. In the illustrated embodiment, a first longitudinal axis 16 of the first mold piece 12 and a second longitudinal axis 18 of the second mold piece 14 are aligned to be substantially parallel and collinear. Bores 20 and 22 extend along the entire length of first mold piece 12 and second mold piece 14, respectively. When assembled together, the first mold piece 12, having bore 20 aligned substantially along axis 16, and the second mold piece 14 having bore 22 aligned substantially along axis 18, the pieces and bores together define variable-length chamber 24. It will be understood that longitudinal axes 16 and 18 need not be collinear, and that in alternative embodiments longitudinal axes 16 and 18 need not be aligned, and may assume different orientations with respect to each other. Similarly, it will be understood that in alternative embodiments, variable-length chamber 24 may comprise a curve or an angle. When connected to the mold pieces 12 and 14, extension shafts 25 may be used to attach the mold 10-1 to a blow-molding machine (not shown).

The variable-length chamber 24 has a length "L" defined by the distance between lines 26 and 28. The position of line 28, which intersects the end 30 of mold piece 14, moves with the position of mold piece 14 and in particular with the position of end 30. Mold piece 14 may be positioned as desired, such positioning effective to position a portion of mold piece 14 within bore 20 to provide a variable-length chamber 24 of a desired length L. Different positions of mold piece 14 and mold piece end 30 are indicated by dotted lines, corresponding to different variable-length chamber lengths L1 and L2 determined by the separations between line 26 and the alternative positions of line 28 as the position of mold piece 14 is changed. After positioning, mold piece 14 remains in position during use of the mold to manufacture an inflatable member. In preferred embodiments, mold piece 14 is firmly locked into position to insure that it maintains the proper position throughout the manufacturing process.

The variable-length chamber 24 is effective to shape and form a central balloon portion of an inflatable member formed with an adjustable length mold assembly of the invention. The length L of a variable-length chamber in a particular configuration of an adjustable length mold assembly determines the length of the central balloon portion of an inflatable member, and so affects the overall cross-sectional configuration of an inflatable member made from that mold. As is shown in FIG. 1, the length of chamber 24 may be varied by effecting longitudinal movement of first mold piece 12, of second mold piece 14, or of both mold pieces.

Thus, length L of a variable-length chamber in an adjustable length mold assembly of the present invention can be adjusted to adopt a variety of desired lengths at different times, allowing the use of a single mold assembly for the manufacture of a variety of inflatable members having balloon portions of differing lengths. An inflatable member having, for example, a central balloon portion of length L1, may be made with adjustable length mold assembly 10-1 when mold piece 14 is positioned so that variable-length chamber 24 has the desired length L1, and, after mold piece 14 has been repositioned so that variable-length chamber 24 has a different desired length L2, the same adjustable length mold assembly 10-1 may then be used to make an inflatable member having a central balloon portion of a desired length L2. These possible positions of mold piece 14 are indicated by the different lengths L, L1 and L2 for variable length chamber 24 shown in FIG. 1A.

Second mold piece 14 is sized and shaped to allow a sliding fit within bore 20 of first mold piece 12 effective to allow second mold piece 14 to fit snugly and to slide longitudinally within bore 20. In embodiments of the invention, the outer diameter of second mold piece 14 is nearly the same as, but very slightly less than, the inner diameter of bore 20 of first mold piece 12. It will be understood, however, that the fit between the outer diameter of second mold piece 14 and the inner diameter of bore 20 need not be exceedingly tight, and that there may be wide tolerances for an acceptable sliding fit between the pieces.

The application of heat to tubing or to the adjustable length mold assemblies of the invention aids in the formation of inflatable members. Heat may be applied to the mold or to a parison within a mold by any suitable means, including use of hot fluids such as hot gases and hot liquids, electrical conduction, electrical induction, radiation, and other means.

A parison of material suitable for the manufacture of an inflatable member may be inserted into the device of FIG. 1 to lie within bores 20 and 22. A parison is typically made of materials that have a softening temperature, which may comprise a range of temperatures, above which the parison becomes soft and expandable, below which the parison hardens and is substantially not expandable. Direct or indirect application of heat to the parison, as, for example, by heating mold piece 12, preferably between lines 26 and 28, is effective to soften the parison, while applying pressure to the inside of the parison, as may be accomplished by filling the parison with a pressurized fluid, is effective to produce a bulging of the softened parison within the variable-length chamber 24. The size and shape, including particularly the length of a balloon portion of the inflatable member will be determined by the size and shape of the variable-length chamber 24. Adjustment of the length L between lines 26 and 28 provides a variable-length chamber effective to form an inflatable member with a balloon portion of the desired length. The application of effective amounts of heat and pressure are effective to cause at least a portion of the parison to expand and contact an inner surface of the adjustable length mold assembly.

When an inflatable member is formed by heating, applying pressure, and optionally applying tension and/or torque to a parison within a mold of the invention, at least a portion of the inner surface of the adjustable length mold assembly constrains the expansion of the parison, and shapes the expanded portion, so that, upon cooling the expanded portion of the parison retains the length and shape imposed by the adjustable length mold assembly. In a preferred embodiment, heat is applied to at least a portion of the parison lying within the variable-length chamber 24, and the shape, size and length of a balloon portion is determined by the variable-length chamber 24. Such application of heat and pressure to at least a portion of the parison, and optionally application of tension and/or torque to the parison, is effective to cause at least a portion of the parison to expand within the variable-length chamber, where the length and geometry of the chamber constrains the expansion of the parison and so determines its length and shape. Following application of heat and pressure, cooling helps to insure that the balloon maintains the proper shape, size, and length following its formation. Such determination of the length and shape of a parison may be effected with each and every embodiment of the adjustable length mold assembly of the present invention.

After the manufacture of an inflatable member, the device of FIG. 1 may be disassembled for removal of the inflatable member by longitudinal movement of the mold pieces so as to increase the separation between lines 26 and 28 until end 30 is outside the bore 20 of the first mold piece 12.

FIG. 1B is a transverse cross-sectional view, with the line of cross-section being line 1B—1B of FIG. 1A, of an adjustable length mold assembly 10-1 showing first mold piece 12, second mold piece 14, and bore 22 which is substantially collinear with bore 20 (shown in FIG. 1A).

Second mold piece 14 is adapted to move so that portions of second mold piece 14 may move within first mold piece 12. Such motion may be effected manually, mechanically, electrically, hydraulically or otherwise. A mechanism adapted to effect such motion, for example, to move a mold piece to a desired position, is termed a positioner. In embodiments of the invention, a positioner may also secure or lock a mold piece into a desired position in addition to moving a mold piece to a desired position.

The adjustable length mold assemblies of the invention may further comprise positioners. It will be understood that a variety of suitable mechanisms effective to position a first mold piece 12 and a second mold piece 14 with respect to each other, so as to provide a desired length to variable-length chamber 24, can be used for the practice of the invention. Positioners may be effective to serve multiple functions, including effecting the movement of pieces of the adjustable length mold assembly, limiting the movement of one or a plurality of the pieces of the adjustable length mold assembly, and locking or securing the pieces of the adjustable length mold assembly in a desired position. The positioners of the invention may comprise manual, mechanical, electrical, electromechanical, electromagnetic, hydraulic, and other positioners, as is illustrated in FIG. 2. In addition, the devices of the invention may comprise locking mechanisms. In one embodiment, the positioners also comprise locking mechanisms; in other embodiments, the locking mechanisms are separate mechanisms independent of the positioners.

In FIG. 1, FIG. 2 and the following figures, like elements are indicated by like reference numbers. FIG. 2 illustrates an adjustable length mold assembly 10-2 configured with a positioner 32 for varying the length of chamber 24 by effecting longitudinal movement of second mold piece 14. As in the adjustable length mold assembly of FIG. 1, a first mold piece 12 fits together with a second mold piece 14, the mold pieces lying along longitudinal axes 16 and 18, so that bores 20 and 22 are substantially collinear. Variable-length chamber 24 has a length defined by the distance between lines 26 and 28, where 28 aligns with the end 30 of second mold piece 14. Positioner 32 may comprise a motor, a servo, a piston, a solenoid, a spring, a lever, a counterweight, a gear, or other device. Preferably, positioner 32 comprises an electromagnetic positioner, such as an electric motor, a stepper motor, servo, solenoid, or other electromotive device, or a hydraulic positioner, including liquid or gas hydraulic devices known in the art.

The positioner 32 shown in FIG. 2A comprises a solenoid 33 operably connected by solenoid shaft 34 to second mold piece 14 effective to position second mold piece 14 in a desired position. Activation of solenoid 33 is effective to cause longitudinal motion of solenoid shaft 34 effective to induce and direct movement of second mold piece 14 to a desired position. In addition, it will be understood by one of ordinary skill in the art that first mold piece 12, or both first mold piece 12 and second mold piece 14, may also be operably connected to a positioner 32, such as solenoid 33, or other positioning device, and so be moved in order to adjust the length L to a desired length and to provide a variable-length chamber 24 of a desired length.

Figure 2B:
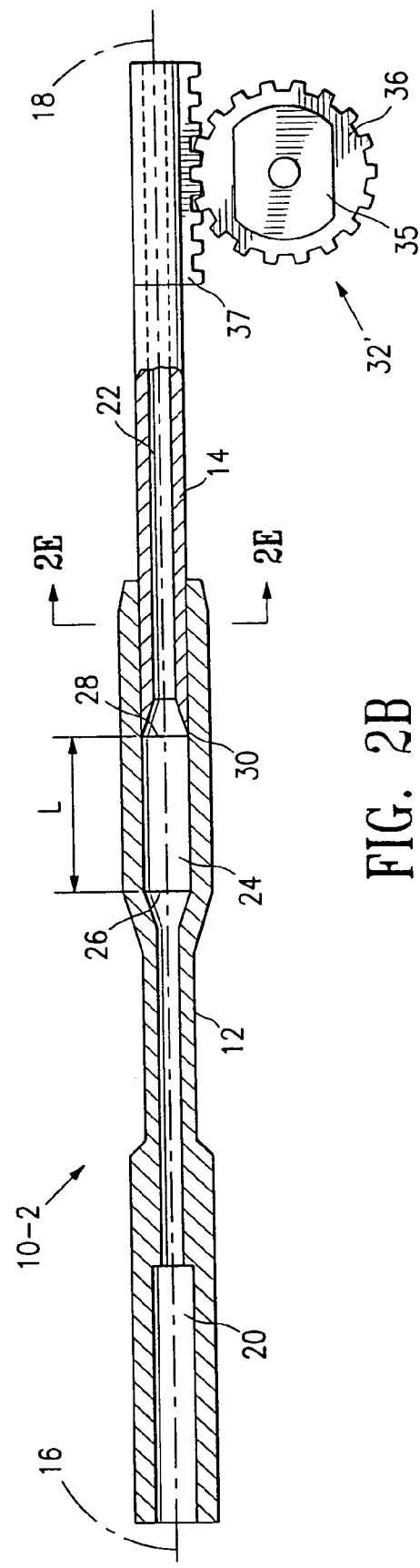
FIG. 2B illustrates a partial longitudinal cross-sectional view of an adjustable length mold assembly embodying features of the invention having mechanical positioner that is a stepper motor.

The positioner 32' shown in FIG. 2B comprises a stepper motor 35 operably connected to pinion gear 36 and a rack gear 37, the gears together forming a rack and pinion mechanism effective to translate rotary motion of the stepper motor 35 and pinion gear 36 into longitudinal motion of the rack gear 37. Rack gear 37 may be operably connected to second mold piece 14, as shown, so that, as stepper motor 35 rotates pinion gear 36, pinion gear 36 is effective to move rack gear 37 in a longitudinal direction, rack gear 37 being operably attached to second mold piece 14, the motion of rack gear 37 being effective to move second mold piece 14 to a desired position. It will be understood that a cable, belt, chain, a chain and pulley, lever, or other mechanisms known in the art could also be used with a stepper motor to position second mold piece 14.

The positioner 32" shown in FIG. 2C comprises a hydraulic positioner 38 with shaft 34' operably connected to second mold piece 14 effective to position second mold piece 14 in a desired position.

Figure 2D:
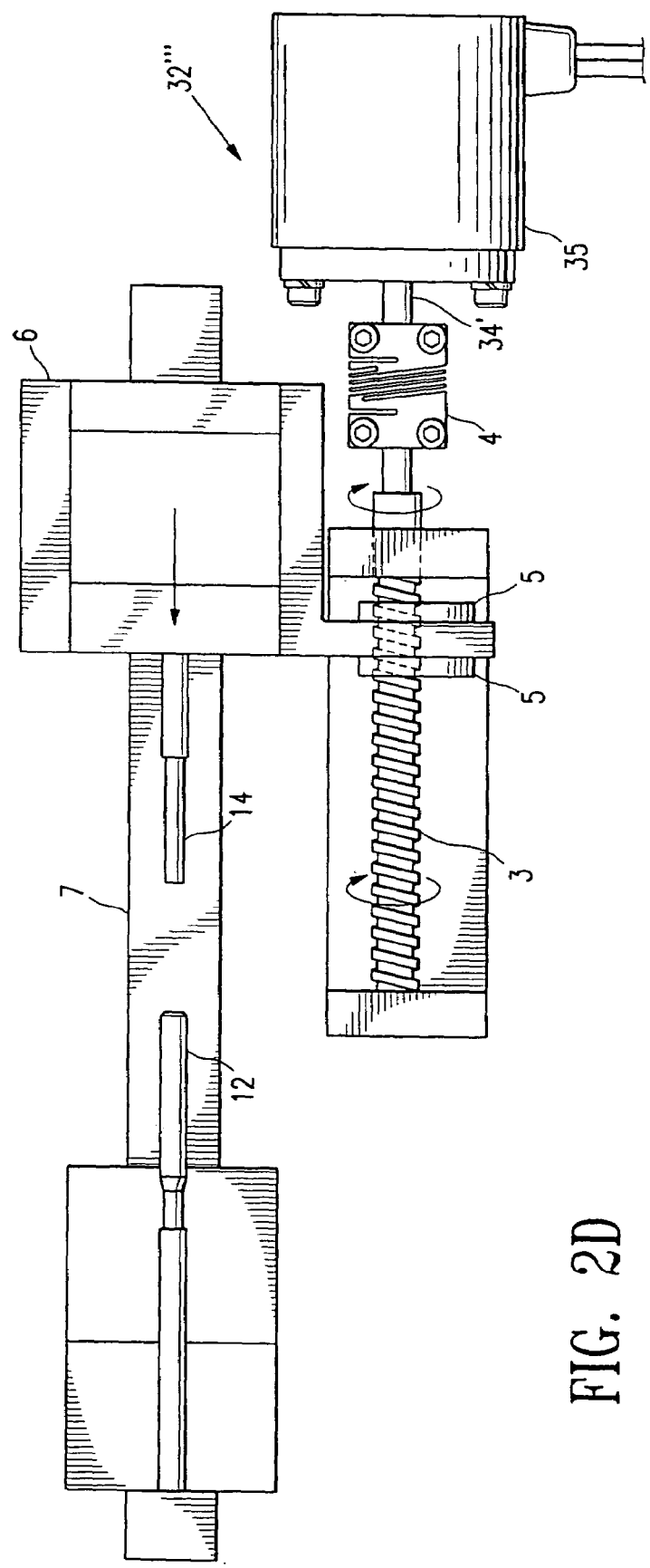
FIG. 2D is a top view of an adjustable length mold assembly embodying features of the invention having a mechanical positioner comprising a stepper motor driving a screw drive.

FIG. 2D shows a positioner 32'" comprising a stepper motor 35, with a stepper motor shaft 34' linked to a screw drive 3 via a coupler 4. Rotation of the screw drive 3 within threaded housing 5 is effective to move carriage 6 along slide 7. Second mold piece 14 is mounted to carriage 6, and so second mold piece 14 is placed in a desired position within first mold piece 12 by rotation of the stepper motor 35. When rotation of the stepper motor 35 ceases, further motion of second mold piece 14 is prevented by the screw drive 3 and threaded housing 5. Thus, in this example, the positioner 32'" is also effective to act as a brake or stop, locking the pieces in place after moving them into their desired positions.

The positioners 32, 32', 32" and 32'" illustrated in FIG. 2 are not the only positioners contemplated in the invention. It will be understood by one of ordinary skill in the art that a variety of mechanisms known to the art are capable of moving second mold piece 14 to a desired position, and that any mechanism capable of placing second mold piece 14 in a proper location with respect to first mold piece 12 (or of placing first mold piece 12 in a proper location with respect to second mold piece 14) is suitable for use as a positioner.

FIG. 2E shows a transverse cross-section of adjustable length mold assembly 10-2 along line 2E—2E of FIGS. 2A, 2B, and 2C. As shown, first mold piece 12 (defining bore 20) and second mold piece 14 (defining bore 22) together enclose and define variable-length chamber 24, as shown in FIGS. 2A, 2B, and 2C.

The length of variable-length chamber 24 may be adjusted, for example, by longitudinal motion of second mold piece 14, so that the end 30 of second mold piece 14 moves with respect to first mold piece 12, in particular, with respect to line 26 through first mold piece 12. Such adjustments provide for a plurality of lengths separating lines 26 and 28, thus making possible the manufacture of inflatable members of a plurality of balloon lengths. A parison of material suitable for the manufacture of an inflatable member may be inserted into the device of FIG. 2 to lie within bores 20 and 22. Application of heat, as, for example, by heating first mold piece 12, preferably between lines 26 and 28, and preferably while applying pressure to the inside of the parison, as may be accomplished by filling the parison with a pressurized gas or liquid, and optionally also applying tension and/or torque to the parison, is effective to produce expansion of the parison within the variable-length chamber 24, where the length and geometry of the chamber constrains the expansion of the parison and so determines its length and shape, thus providing an inflatable member with a balloon portion of the desired length and shape. Subsequent cooling helps to insure that the balloon maintains the proper shape, size, and length following its formation. Following formation of an inflatable member, the device of FIG. 2 may be disassembled for removal of the inflatable member by longitudinal movement of the mold pieces so as to increase the separation between lines 26 and 28 until end 30 is outside the bore 20 of the first mold piece 12.

A positioner may comprise a screw, as illustrated in FIG. 3. The adjustable length mold assembly 10-3 illustrated in FIGS. 3A and 3B comprises a first mold piece 40, a second mold piece 41, and an internal mold piece 42 with bore 43, a proximal end 44, and a threaded end 45. First mold piece 40, with distal end 46, has a bore 47 with threaded surface 48. Mold pieces 40, 41, and 42 are generally disposed along longitudinal axis 50. Threaded end 45 of internal mold piece 42 may be entirely or partly enclosed within distal end 46 of first mold piece 40, or may partly extend from and out of distal end 46. In any case, at least a portion of threaded end 45 of internal mold piece 42 is threadably engaged with threaded surface 48 of first mold piece 40 effective to produce longitudinal motion when either or both internal mold piece 42 and first mold piece 40 rotate about longitudinal axis 50. Such motion of internal mold piece 40 along longitudinal axis 50 is effective to change the length of variable-length chamber 52, defined by the distance between the end 54 of second mold piece 41, at line 56, and the end 44 of internal mold piece 42, at line 58. Chamber 52 is continuous with bores 43 of internal mold piece 42, 47 of first mold piece 40 and bore 60 of the second mold piece 41. Rotation about longitudinal axis 50 may be effected manually, mechanically, electrically, hydraulically, or otherwise. For example, a screwdriver or other flat tool may be inserted into slot 61 and rotated to effect rotation and resulting longitudinal movement of internal mold piece 42. Alternatively, a motor or other mechanical drive may be operably connected to internal mold piece 42 and used to rotate internal mold piece 42, such rotation being effective to produce longitudinal movement of the internal mold piece 42 within first mold piece 40 and so to vary the length of the variable-length chamber 52.

Prior to use of an adjustable length mold assembly in the manufacture of an inflatable member, the length of variable-length chamber 52 is adjusted, for example, by rotation of internal mold piece 42. A parison of material suitable for the manufacture of an inflatable member may be inserted into the device of FIG. 3 via bores 43, 47 and 60. Application of heat, as, for example, by heating mold piece 40, preferably in the region adjacent to and between lines 56 and 58, while applying pressure to the inside of the parison, as may be accomplished by filling the parison with a pressurized gas or liquid, and optionally applying tension and/or torque to the parison, is effective to produce expansion of the parison within the variable-length chamber 52 so as to cause the parison to expand within the variable-length chamber, where the length and geometry of the chamber constrains the expansion of the parison and so determines its length and shape, thus providing an inflatable member with a balloon portion of the desired length and shape.

After its use in the manufacture of an inflatable member, the assembly of FIG. 3 may be separated along line 56 to allow removal of the inflatable member. The adjustable length mold assembly may then be reassembled with the internal mold piece 42 in a different desired position, and a new inflatable member of a different length made by the same mold 10-3.

A transverse cross-sectional view of the adjustable length mold assembly 10-3 is shown in FIG. 3B, with the cross-section taken along line 3B—3B intersecting the slot 61. The first mold piece 40 is illustrated with one direction of cross-hatching, the internal mold piece 42 with another direction of cross-hatching, with the depth of threads 48 (on an internal surface of first mold piece 40) and threads 45 (on an end of internal mold piece 42) indicated by a dotted line. Bore 43 of internal mold piece 42 is also shown in FIG. 3B.

A positioner may comprise a bar, slotted bar, sleeve (including a spring) or other spacer, as illustrated in FIG. 4. The adjustable length mold assembly 10-4 illustrated in FIG. 4, as shown in FIG. 4A, comprises a first mold piece 12 and a second mold piece 14, both mold pieces disposed around longitudinal axes 16 and 18, these longitudinal axes being generally collinear when the pieces are assembled together. Bores 20 and 22 in mold pieces 12 and 14, respectively, provide access to variable-length chamber 24, chamber 24 being a variable-length portion of bore 20 that is continuous with bore 22. The length of variable-length chamber 24 is defined by the distance between lines 26 and 28, second mold piece 14 having a proximal end 30, the line 28 coincident with end 30, and a distal end portion 63. Second mold piece distal end portion 63 is effective to act as a stop. First mold piece 12 has end 64, effective to contact sleeve 65, which is effective to define and/or maintain a desired separation between first mold piece end 64 and second mold piece distal end portion 63. It will be understood that the sleeve length may be adjusted, or that the position of distal end portion 63, effective to act as a stop, may be adjusted, either or both adjustments being effective to define and/or maintain a desired separation between first mold piece end 64 and second mold piece distal end portion 63. Alternatively, distal end portion 63 may be contacted by a stop that is external to the mold pieces shown, but is instead fixedly attached to a support or other fixture, such as a bench, table, or bracket, that is near to, or connected to, the adjustable length mold assembly of the invention.

A transverse cross-sectional view of the adjustable length mold assembly 10-4 with a sleeve 65, taken along line 4B—4B, is shown in FIG. 4B. Stop 63 as shown in FIG. 4B has a larger radial dimension than sleeve 65, which in turn has a larger radial dimension than second mold piece 14, which sleeve 65 surrounds. It will be understood that any radial dimension of stop 63 that is effective to contact and position sleeve 65 is suitable, and that stop 63 and sleeve 65 may have slots or other irregularities so that neither stop 63 nor sleeve 65 need have the same radial dimension at all angles around a longitudinal axis.

Movement of second mold piece 14 along longitudinal axis 18 is effective to change the length of variable-length chamber 24. Such movement may be effected manually, mechanically, electrically, hydraulically or otherwise. Line 28 is defined by and follows the end 30 of the second mold piece 14. A sleeve 65 limits movement of line 28 in a longitudinal direction towards line 26. It will be understood by one of ordinary skill in the art that sleeve 65 may be made in any desired length. A plurality of sleeves 65 of differing lengths, examples of which are shown in FIGS. 4C-1, 4C-2, and 4C-3, are each individually effective to provide a defined distance L between lines 26 and 28 when placed in contact with both a distal end portion 63 (which acts as a stop) and a first mold piece end 64. Thus, a plurality of sleeves 65 are together effective to provide a plurality of defined distances L between lines 26 and 28, and so are effective to provide a plurality of chamber lengths to chamber 24 formed by the assembly of the mold parts shown in FIG. 4A. Alternatively, an adjustable sleeve, such as, for example, telescoping sleeve shown in 4D, with inner sleeve member 66 and outer sleeve member 67, held in position by set-screw 68, is effective to define a plurality of lengths, and is suitable for the practice of the invention. It will be understood by one of ordinary skill in the art that the adjustable sleeves as in 4D may comprise a variety of adjustable sleeves, such as threaded tubes attached and threaded to each other whereby counter-rotation of the tubes is effective to adjust the overall length of the sleeve, or other adjustable sleeves known to the art, and which are all also suitable for the practice of the invention.

A parison of material suitable for the manufacture of an inflatable member may be inserted into the device of FIG. 4 via bores 20 and 22. Application of heat to the parison, as, for example, by heating mold piece 12, preferably between lines 26 and 28, effective to soften the parison, while applying pressure to the inside of the parison, as may be accomplished, for example, by filling the parison with a pressurized gas or liquid, and optionally also applying tension and/or torque to the parison, is effective to produce expansion of the parison within the variable-length chamber 24, where the length and geometry of the variable-length chamber 24 constrains the expansion of the parison and so determines its length and shape, thus providing an inflatable member with a balloon portion of the desired length and shape. The first and second mold pieces 12 and 14 separate to allow removal of the inflatable member after its formation. The adjustable length mold assembly may then be reassembled, with, for example, a different sleeve 65 of different length, or an adjustable sleeve adjusted to a different length, and a new inflatable member of a different length made by the same mold 10-4.

Figure 5A:
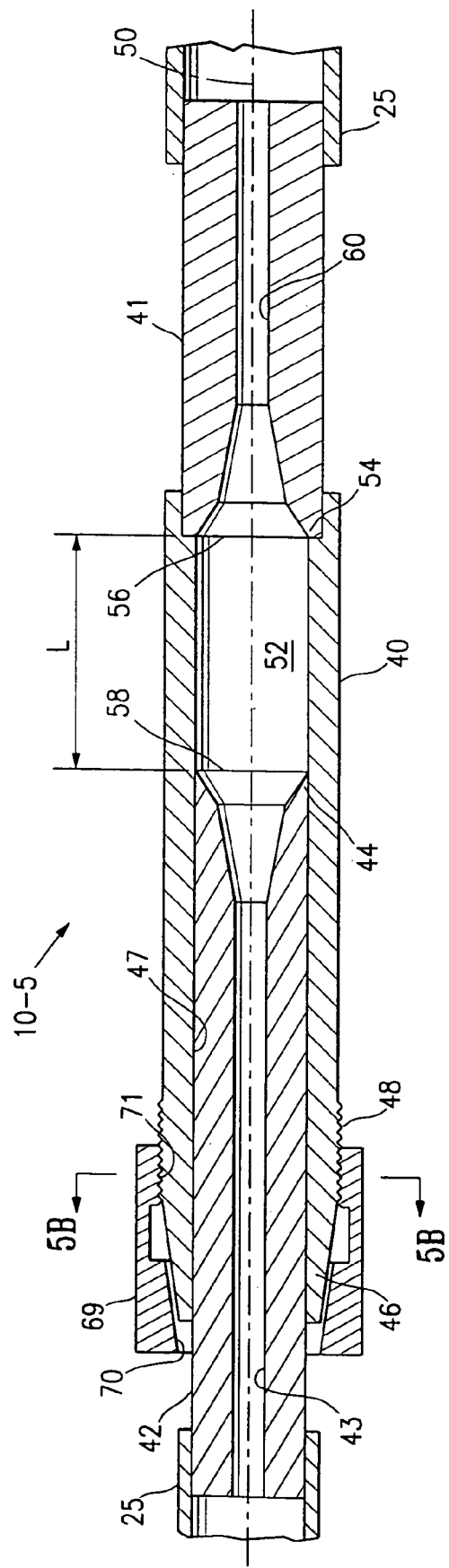
FIG. 5A illustrates a longitudinal cross-sectional view of an adjustable length mold assembly embodying features of the invention, the mold assembly having a locking mechanism.

After configuring the length of a variable-length chamber (such as 24 in FIGS. 1, 2 and 4, and 52 in FIG. 3) to have a desired length, it is preferred to secure the mold pieces with a locking mechanism so that the length of the chamber does not change during manufacture of an inflatable element. A locking mechanism may comprise a set screw, a clamp, a stop combined with a mechanism for urging a part against the stop (such as a spring), an orifice, opening or depression adapted to receive a detent, bar, ball, or other such member, or other locking mechanisms known in the art, as illustrated in FIG. 5. The adjustable length mold assembly 10-5 illustrated in FIG. 5, as shown in FIG. 5A, comprises a first mold piece 40, a second mold piece 41, and an internal mold piece 42 with bore 43, and a proximal end 44. First mold piece 40, with distal end 46, which is tapered and has threads 48, has bore 47 sized to receive inner mold piece 42. Mold pieces 40, 41, and 42 are generally disposed along longitudinal axis 50. Variable-length chamber 52 is continuous with bore 47 of first mold piece 40, bore 60 of second mold piece 41, and bore 43 of internal mold piece 42. The length L of variable-length chamber 52 is defined by the distance between the end 54 of second mold piece 41, at line 56, and the end 44 of internal mold piece 42, at line 58.

Internal mold piece 42 is adapted to move along longitudinal axis 50, effective to produce longitudinal movement of the internal mold piece 42 within first mold piece 40 and so to vary the length of the variable-length chamber 52. Such motion may be effected manually, mechanically, electrically, hydraulically or otherwise.

Prior to use of an adjustable length mold assembly in the manufacture of an inflatable member, after adjustment of the length of variable-length chamber 52, the length of the variable-length chamber 52 may be fixed by a locking mechanism. It will be understood that any locking mechanism effective to prevent alteration in the length of the variable-length chamber during manufacture of an inflatable member with an adjustable length mold assembly of the invention is a suitable locking mechanism. A positioner may comprise a locking mechanism where the positioner may be used to lock a mold piece in position as well as to move a mold piece to a desired position. For example, rotation of a screw-drive or worm gear is effective to move a mold piece, as may be effected by, for example, a stepper motor, and is effective to lock a mold piece into position when the screw or gear is not made to rotate or is prevented from rotating.

An example of locking mechanism suitable for use in the invention is illustrated in FIG. 5A, showing locking mechanism 69 having tapered inner surface 70 and threaded surface 71 mounted upon the distal portion 46 of first mold piece 40. Engagement of threads 71 of locking mechanism 69 with threads 48 of the first mold piece 40, is, upon rotation, effective to produce longitudinal motion of piece 69 relative to the first mold piece 40. Movement of locking mechanism 69 in a proximal direction, towards variable-length chamber 52 is effective to bring inner face 70 in contact with distal portion 46; further motion or pressure applied in the same direction is effective to compress distal portion 46 effective to lock internal mold piece 42 into position.

A parison of material suitable for the manufacture of an inflatable member may be inserted into the device of FIG. 5 via bores 60 and 43. Application of heat, as, for example, by heating mold piece 40, preferably in the region adjacent to and between lines 56 and 58, while applying pressure to the inside of the parison, as may be accomplished by filling the parison with a pressurized gas or liquid, and optionally also applying tension and/or torque to the parison, is effective to produce expansion of the parison within the variable-length chamber 52 so as to cause the parison to expand within the variable-length chamber, where the length and geometry of the chamber constrains the expansion of the parison and so determines its length and shape, thus providing an inflatable member with a balloon portion of the desired length and shape.

After its use in the manufacture of an inflatable member, the device of FIG. 5 may be separated along line 56 to allow removal of the inflatable member. Release of the pressure due to locking mechanism 69 is effective to allow the movement and repositioning of internal mold piece 42. The adjustable length mold assembly may then be reassembled with the internal mold piece 42 in a different desired position, the locking mechanism 69 tightened to lock internal mold piece 42 into its new desired position, and a new inflatable member of a different length made by the same mold 10-5.

Figure 5B:
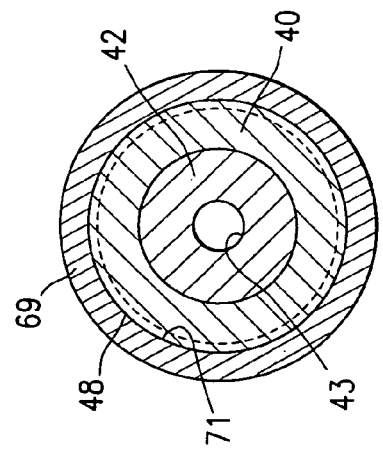
FIG. 5B is a transverse cross-sectional view of the adjustable length mold assembly of FIG. 5A taken along line 5B—5B.

A transverse cross-sectional view of the adjustable length mold assembly 10-5 is shown in FIG. 5B, with the cross-section taken along line 5B—5B intersecting threads 48 and 71. The first mold piece 40 is illustrated with one direction of cross-hatching, the internal mold piece 42 with another direction of cross-hatching, and locking mechanism 69 with a third style of cross-hatching, while the depth of the threads is shown by a dotted line. Bore 43 of internal mold piece 42 is also shown in FIG. 5B.

Inflatable members of different lengths may be formed by the use of the adjustable length mold assemblies of the invention. Such inflatable members may have similar cross-sectional profiles but will have balloon portions of different lengths corresponding to the different lengths L falling between lines 26 and 28 in FIGS. 1, 2, and 4, and between lines 56 and 58 in FIGS. 3 and 5. FIG. 1A shows an example of different lengths L, L1, and L2 corresponding to different lengths of variable-length chamber 24.

Bores of mold pieces of adjustable length mold assemblies of the invention comprise tapers connecting bore regions of different diameters. Such tapers may comprise regions with flat cross-sections as illustrated in FIGS. 1–5 where the taper comprises substantially a portion of a cone. Alternatively, the tapers may comprise curved cross-sections, combined curved and flat cross-sections, or cross-sections of other kinds. For example, tapers may comprise two or more portions of cones, so that the taper cross-section comprises a plurality of flat regions that intersect other regions of the bore at different angles. Such tapers are effective to form tapered ends of balloon portions of inflatable members formed by the adjustable length mold assemblies of the invention.

Figure 6:
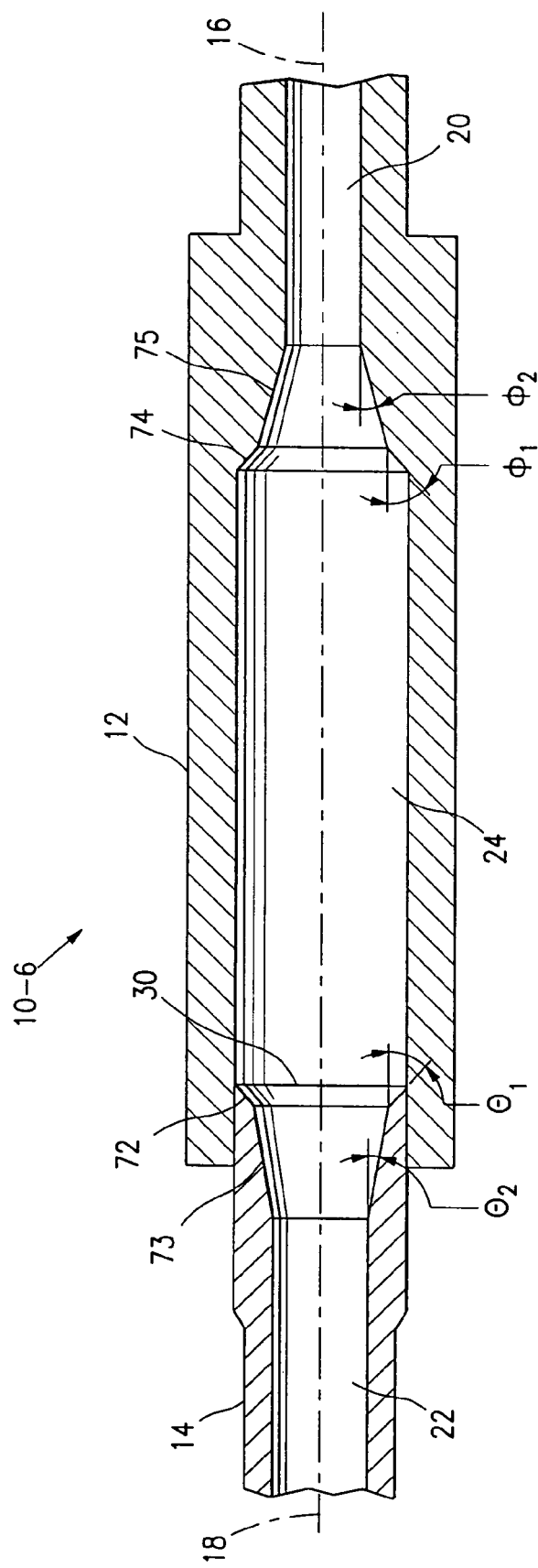
FIG. 6 is a longitudinal cross-sectional view of an adjustable length mold assembly embodying features of the invention having multiply-sloped tapers at either end of the variable-length chamber of the mold assembly.

FIG. 6 illustrates an adjustable length mold assembly 10-6 embodying features of the invention, comprising tapered bores 20 and 22 each with two differently-angled portions. Assembly 10-6 includes a first mold piece 12 and second mold piece 14. The mold pieces 12 and 14 may be assembled together as shown in FIG. 6, with the first longitudinal axis 16 of the first mold piece 12 and the second longitudinal axis 18 of the second mold piece 14 aligned to be substantially parallel and collinear. First mold piece 12 has bore 20 aligned substantially along axis 16, and the second mold piece 14 has bore 22 aligned substantially along axis 18, the pieces and bores together define variable-length chamber 24.

The end 30 of second mold piece 14 is adjacent to the taper region of bore 22, where the bore adjacent 30 defines the taper region comprising two portions 72 and 73 having different angles $\theta_1$ and $\theta_2$ with respect to longitudinal axis 18. Similarly, bore 20 of first mold piece 12 has a taper region comprised of two portions 74 and 75 having different angles $\phi_1$ and $\phi_2$ with respect to longitudinal axis 16. Angle $\theta_1$ may be, but need not be, equal to one or both of angles $\phi_1$ and $\phi_2$; similarly, angle $\theta_2$ may be, but need not be, equal to one or both of angles $\phi_1$ and $\phi_2$. Balloons formed with adjustable length mold assembly 10-6 will have a central balloon portion shaped to conform to the taper portions. It will be understood by one of ordinary skill in the art that the number of taper portions in such molds may vary, and is not limited to a particular number of such portions. In addition, it will be understood that tapers 72, 73, 74, and 75 may differ one from the other, and in particular, taper 72 need not be the same as taper 74 or taper 75, and taper 73 need not be the same as taper 74 or taper 75.

Adjustable length mold assemblies of the invention can be used to form inflatable members having balloons having any desired configuration. For example, an adjustable length mold assembly of the invention may be used to produce inflatable members having non-lobed balloons or having lobed balloons. The presence and number of lobes on a balloon portion of an inflatable member affects the folding of the balloon, an important aspect of an inflatable member relating to the insertion properties of the completed catheter. The cross-sectional configuration of the mold pieces of the adjustable length mold assembly in large part determines the shape of the inflatable member. Multiply-lobed balloons are generally more easily folded than are balloons without lobes. Several representative mold cross-sections are illustrated in FIG. 7A through 7D, the cross-sections being taken along a line corresponding to line 26 in the first mold piece of FIGS. 1, 2 and 4, and line 56 in the first mold piece of FIGS. 3 and 5. The mold illustrated in FIG. 6 can also have as a cross-section any of the cross-sections illustrated in FIG. 7.

Figure 7B:
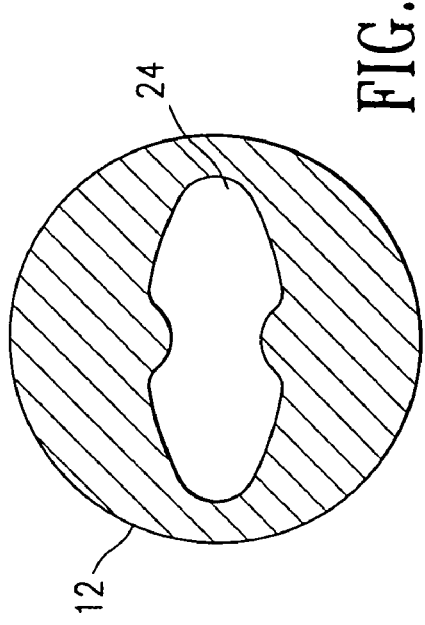
FIG. 7B illustrates a transverse cross-section of an adjustable length mold assembly embodying features of the invention having a bore with a lobed cross-section.
Figure 7D:
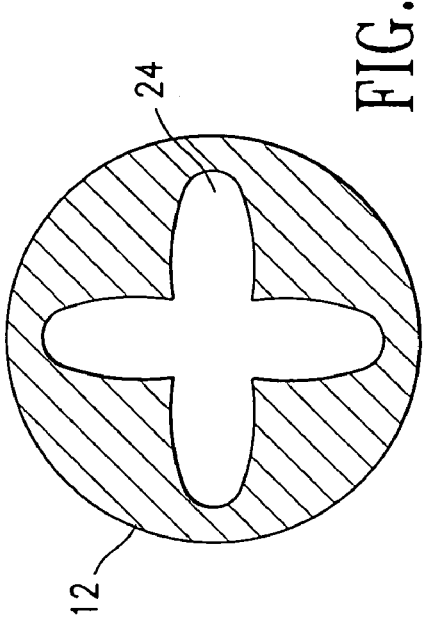
FIG. 7D illustrates a transverse cross-section of an adjustable length mold assembly embodying features of the invention having a bore with a four-lobed cross-section.
Figure 7A:
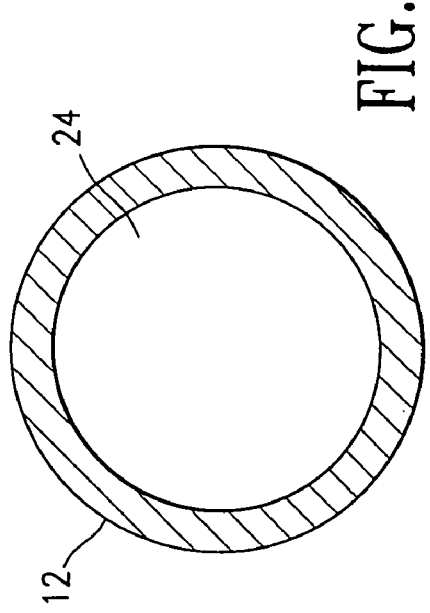
FIG. 7A illustrates a transverse cross-section of an adjustable length mold assembly embodying features of the invention having a bore with a substantially circular cross-section.
Figure 7C:
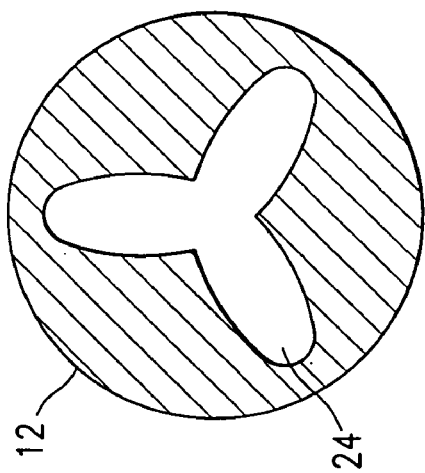
FIG. 7C illustrates a transverse cross-section of an adjustable length mold assembly embodying features of the invention having a bore with three-lobed cross-section.

A cross-section of a mold suitable for forming a generally cylindrical balloon, without lobes, is presented in FIG. 7A, which illustrates a cross-section of a mold part with a substantially circular inner-bore configuration. A cross-section of a mold suitable for forming a doubly-lobed balloon is presented in FIG. 7B, which illustrates a cross-section of a mold part with a generally elliptical, or pinched-elliptical, inner-bore configuration. A cross-section of a mold assembly suitable for forming a triply-lobed balloon is presented in FIG. 7C, and a cross-section of a mold assembly suitable for forming a balloon with four lobes is presented in FIG. 7D.

The adjustable length mold assemblies described above may be made from any suitable material, or combination of suitable materials, suitable materials including glass, ceramic, high temperature plastic, and metal. Preferred mold pieces are made of stainless steel, and most preferred mold pieces are made of high grade stainless steel.

Inflatable members that may be made using the variable length molds of the invention include angioplasty and stent delivery balloons. Angioplasty and stent delivery balloons are typically made of polymeric materials. In general, the polymeric material is extruded into tubular shapes or parisons. The extruded parison is then formed into the balloon shape using a blow molding process. Apparatus of the balloon blow molding process comprises a mold, a temperature source, a pressure source, and a tension source. In the balloon molding process, the extruded tubing is placed inside the mold and subsequently, the mold is heated with the temperature source. The tubing may be stretched longitudinally under the influence of the tension source and is expanded under the influence of the pressure source. The mold, being made of a plurality of parts, provides ease of access to the finished inflatable member. The final balloon shape is mostly determined by the geometric design of the mold and the process parameters. The molds are generally made from materials that can be formed into desirable shapes and are geometrically stable at elevated temperatures. The different mold pieces may be fabricated using machining methods consistent with the choice of material and quality requirements.

Examples of cross-sectional profiles of unwrapped balloons in the inflated condition are shown in FIG. 8. FIGS. 8A, 8B and 8C are partial longitudinal cross sectional views of balloons of three different lengths made from one adjustable length mold assembly of the invention.

FIG. 8 illustrates three examples of inflated balloons formed by an adjustable length mold assembly using variable-length chamber settings of different lengths, where the balloons are labeled 76A in FIG. 8A, 76B in FIGS. 8B and 76C in FIG. 8C. The balloons 76A, 76B and 76C include proximal sections 78 and distal sections 80 with a central section 82 located therebetween. In some embodiments of balloon catheters, further portions include proximal and distal intermediate ends, 84 and 86, for receiving a stent (not shown) on all or a portion of a central section 82. It should be noted that, although the other portions do not differ, the central sections 82 differ in length between the balloons shown in FIGS. 8A, 8B and 8C. The proximal and distal sections, 78 and 80, taper down from the central section 82, to the proximal and distal shafts 88 and 90, with angles $\Theta_1$ and $\Theta_2$ with respect to longitudinal axis 92. Taper angle $\Theta_1$ may be, but need not be, equal to taper angle $\Theta_2$. Manufacture of inflatable members, such as balloon catheters, with the adjustable length mold assemblies of the invention, provides balloons with central sections 82 of different lengths but similar proximal and distal sections 78 and 80 and shafts 88 and 90, as shown in FIGS. 8A, 8B and 8C.

Figure 9:
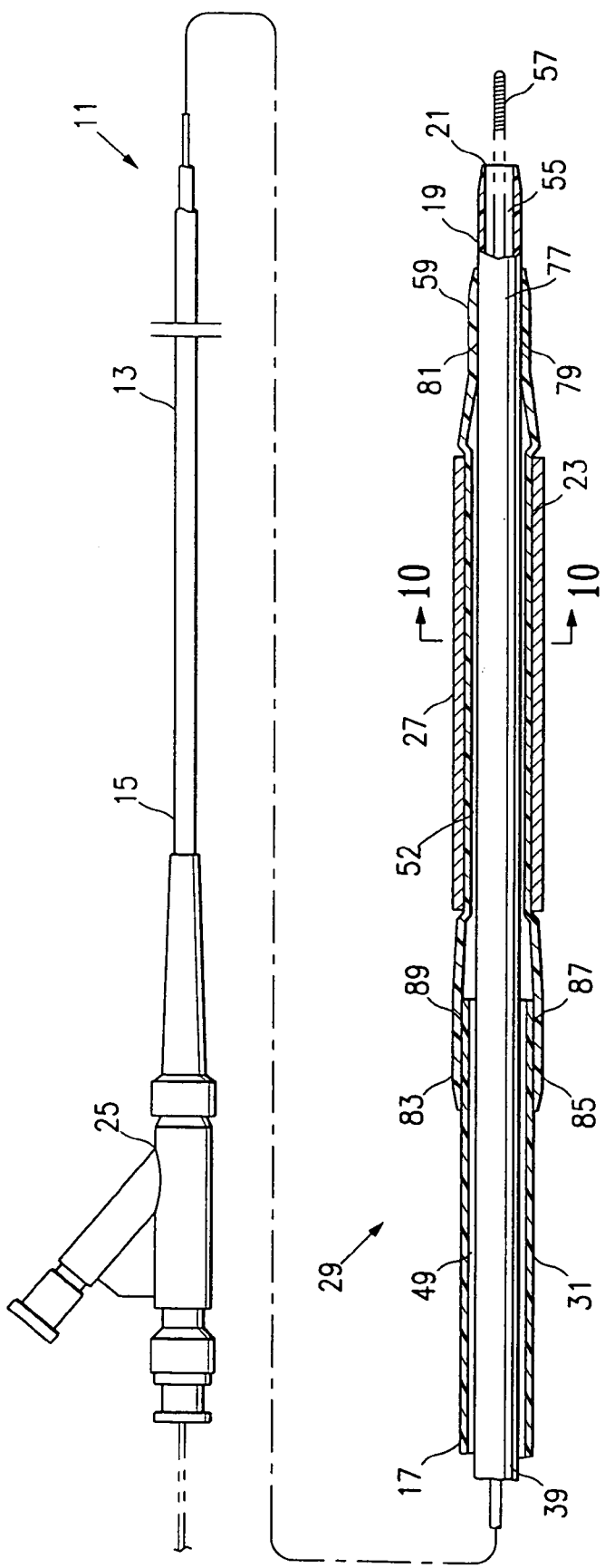
FIG. 9 is a partially cut-away partial cross-sectional view of a balloon catheter comprising an inflatable member produced by an adjustable length mold assembly embodying features of the invention.

The inflatable members produced with the adjustable length mold assemblies of the invention may be used in catheters for medical, veterinary or research purposes. A preferred use is in catheters for human medical treatment, such as, for example, cardiac catheters used in angioplasty or stent delivery for treatment of heart or arterial disorders. FIG. 9 illustrates a balloon catheter 11 generally including an elongated catheter shaft 13 having a proximal section 15 and a distal section 17 with a distal end 19 and a distal tip 21, the inflatable balloon 23 on the distal section 17 of the catheter shaft 13, and an adapter 25 mounted on the proximal section 15 of the catheter shaft 13. In the embodiment illustrated in FIG. 9, the balloon catheter 11 has a stent 27 mounted on the balloon 23 to form a stent delivery catheter system 29. The catheter system 29 is illustrated prior to expansion of the wrapped balloon 23, with the balloon 23 and stent 27 in a low profile, unexpanded state for advancement within the patient.

In the embodiment illustrated in FIG. 9, the catheter shaft 13 has an outer tubular member 31 and an inner tubular member 39 disposed within the outer tubular member 31 and defining, with the outer tubular member, an inflation lumen 49. The inflation lumen 49 is in fluid communication with an interior chamber 51 of the balloon 23. The inner tubular member 39 has an inner lumen 55 extending therein configured to slidably receive a guidewire 57 (shown in phantom) suitable for advancement through a patient's cardiovascular system. A distal extremity 59 of the balloon 23 is sealingly secured to a distal extremity 77 of the inner tubular member 39 to form a distal seal 79 at distal junction 81 and a proximal extremity 83 of the balloon 23 is sealingly secured to a distal extremity 85 of the outer tubular member 31 to form a proximal seal 87 at a proximal junction 89.

Figure 10:
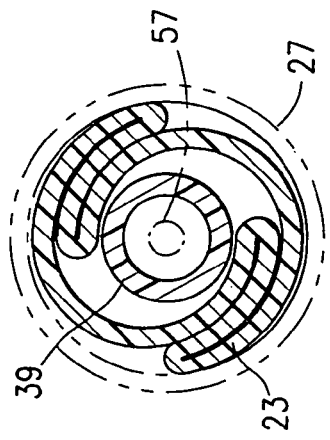
FIG. 10 is a transverse cross sectional view of a folded balloon formed by an adjustable length mold assembly embodying features of the invention.

Inflatable members, such as balloon catheters, or portions thereof, may be folded before inflation to minimize their radial dimension and facilitate their entry into small-diameter tubular regions such as blood vessels. The inclusion of lobes in the design of a balloon facilitates the folding of the balloon. An example of such folding is presented in FIG. 10. FIG. 10 shows a balloon folded for advancement within a patient. The solid lines represent the outer surfaces of the balloon; the dotted lines represent the boundaries of a stent, in unexpanded form, were a stent to be placed on the balloon for delivery to a desired location within a patient. In FIG. 10, inner tubular member 39 is enclosed by folded balloon 23. Shown in dotted lines is a stent 27, in unexpanded condition, capable of being carried by balloon 23 to a desired position within a patient.

It will be understood that the adjustable length mold assemblies of the invention may further comprise other mold pieces in addition to the first mold piece, second mold piece, positioner, locking mechanism, and other pieces described above. For example, the second mold piece may be engaged and held by a support or extension, the support or extension contacting a positioner, a connection to pressurized gas, or other piece. Thus, the second mold piece having an exterior surface configured to be slidably received by the bore of the first mold piece may be a constituent of a second mold group that may also include, among other constituents, a support that is configured to engage and hold the second mold piece.

Such an extension may be useful, for example, for positioning the second mold piece, and may be effective to reduce the possibility of wear or damage to precision surfaces of the second mold piece.

The length of a balloon portion of an inflatable member manufactured using an adjustable length mold assembly of the invention may vary as desired, but in general will be between about 1 mm to about 100 mm in length, preferably between about 2 mm to about 80 mm in length, more preferably between about 5 mm to about 60 mm in length, most preferably between about 7 mm to about 50 mm in length.

Similarly, the range of movement of the inner mold piece within a bore of the outer mold piece may be from between about 1 mm to about 150 mm, preferably from between about 1 mm to about 100 mm, more preferably from between about 5 mm to about 60 mm in length, most preferably from between about 7 mm to about 50 mm in length. As a fraction of the length of a variable-length chamber, the inner mold piece may be adapted to move from about 1% to about 100% of the length of a variable-length chamber, preferably from between about 2% to about 80%, more preferably from between about 5% to about 60% in length, most preferably from between about 7% to about 50% of the length of a variable-length chamber.

The dimensions of the outside diameter of an inflated balloon manufactured by an adjustable length mold assembly of the present invention will be determined by the dimensions of the chamber of the adjustable length mold assembly. Such dimensions may vary depending upon the intended use of the inflatable member, and the desired location of use within the body of a patient. In general, the outside diameters of an inflated balloon for angioplasty and stent delivery may range from about 0.5 mm to about 30 mm, preferably from about 1 mm to about 15 mm, most preferably from about 2 mm to about 10 mm.

It will be understood that the shape and dimensions of the mold pieces used in assembling the adjustable length mold assemblies of the invention may be symmetrical with opposing ends having similar taper angles and dimensions, or may be different. In general, the ends of the balloons produced by the adjustable length mold assemblies of the invention will be symmetrical, with similar or equal taper angles and dimensions. However, in embodiments of the invention, the mold pieces of the adjustable length mold assemblies of the invention have different taper angles and/or different dimensions. Thus, for example, the tapers produced by the variable length molds of the invention may differ at the two ends of the balloons produced by the molds. In addition, by assembling an adjustable length mold assembly from different pieces at different times, one mold assembly may be used at one time to make balloons with symmetrical tapers at each end, and to make balloons with differing tapers at the ends at a different time. Similarly, mold pieces with differing dimensions may be used to produce balloons with balloon portions having different dimensions, such as different diameters at different positions along the length of the balloon.

It will also be understood that features described or illustrated as part of particular embodiments of the adjustable length mold assemblies may also be included or combined with other features of other embodiments of the adjustable length mold assemblies of the invention, as may obvious variants of any of the elements and features of the invention disclosed herein. Thus, while particular forms of the invention have been illustrated and described, it will be apparent that various modifications can be made without departing from the spirit and scope of the invention. Accordingly, it is not intended that the invention be limited, except as by the appended claims.

What is claimed is:

1. A method of forming a catheter inflatable member, comprising
   (a) providing an adjustable length mold assembly, comprising a first mold piece having a first internal chamber defined at least in part by a first internal molding surface which is configured to form a first exterior surface of a first section of a catheter inflatable member formed in the mold and which has an internal shoulder section, and a second mold piece, at least in part slidably disposed within at least a portion of said first mold piece, having a second internal chamber defined at least in part by a second internal molding surface configured to form a second exterior surface of a second section of the catheter inflatable member formed in the mold, the second mold piece having an end with a radial dimension configured to abut the internal shoulder of the first mold piece so that the second mold piece end is effective as a stop, and an internal third mold piece at least in part slidably disposed within at least a portion of the first mold piece and having a third internal chamber defined at least in part by a third internal molding surface configured to form a third exterior surface of a third section of the catheter inflatable member formed in the mold, the internal third mold piece having an end configured to be slidable within the first mold piece to place the third mold piece in a plurality of longitudinal positions therein, and placing the second mold piece end against the internal shoulder of the first mold piece, and adjusting the longitudinal distance between the end of the second mold piece and the end of the third mold piece by sliding the third mold piece within the first mold piece;
   (b) placing a parison within the variable-length chamber defined by the internal molding surfaces of the mold pieces,
   (c) heating the parison to a temperature effective to soften the parison, and
   (d) raising the internal pressure of the parison effective to expand at least a portion of the parison so that at least a portion of the parison contacts the first, second and third internal molding surfaces of the mold, thereby forming the catheter inflatable member; and
   (e) separating the first and second mold pieces to access the inflatable member within the first and third internal chambers, and removing the inflatable member from the mold.

2. The method of claim 1, wherein the parison has a softening temperature and wherein the inflatable member is cooled to a temperature below the softening temperature of the parison.

3. The method of claim 1, further comprising the step of locking the third mold piece into a desired position with respect to the first mold piece.

4. The method of claim 1, further comprising the application of torque to the parison.

5. The method of claim 1, wherein heating the parison comprises heating at least part of the mold.

6. A method of forming an inflatable member, comprising
   (a) providing an adjustable length mold assembly, comprising a first mold piece having a first internal chamber with a first internal molding surface adapted for molding a central cylindrical working surface of an inflatable member, and a second mold piece releaseably connected to the first m old piece and having a second internal chamber with a second internal molding surface adapted for molding a tapered end section of the inflatable member, and an internal third mold piece at least in part slidably disposed within at least a portion of the first mold piece and having a third internal chamber with a third internal molding surface adapted for molding a tapered end section of the inflatable member, and sliding the first and third mold pieces relative to one another to position the third mold piece at a location within the first internal chamber to thereby define the length of the central cylindrical working surface of the inflatable member;

(b) placing a parison within the variable-length chamber defined by the first and second internal molding surfaces of the first and second mold pieces, (c) heating the parison to a temperature effective to soften the parison, (d) raising the internal pressure of the parison effective to expand at least a portion of the parison effective that at least a portion of the parison contacts an inner surface of the chamber, thereby forming an inflatable member; and e) separating the first and second mold pieces, and then removing the inflatable member from the variable-length chamber.

7. A method of forming a balloon catheter, comprising (a) providing an adjustable length mold assembly, comprising a first mold piece having a first internal chamber with a first internal molding surface which is adapted for molding a working surface of a balloon portion of an inflatable member and which has an internal shoulder section, and a second mold piece, having a second internal chamber with a second internal molding surface adapted for molding a tapered end section of the balloon portion of the inflatable member, and an internal third mold piece having a third internal chamber with a third internal molding surface adapted for molding an opposite tapered end section of the balloon portion of the inflatable member, the first, second and third mold pieces being in slidable relation relative to each other and the second mold piece having a surface with a radial dimension configured to abut the internal shoulder of the first mold piece so that the second mold piece end is effective as a stop, and the internal third mold piece having an end configured to be slidable within the first mold piece to place the third mold piece in a plurality of longitudinal positions within the first mold piece, and placing the second mold piece surface against the internal shoulder of the first mold piece, and adjusting the longitudinal distance between the end of the second mold piece and the end of the third mold piece by sliding the third mold piece within the first mold piece;

(b) placing a parison within the variable-length chamber defined by the internal molding surfaces of the mold pieces, (c) heating the parison to a temperature effective to soften the parison, and (d) raising the internal pressure of the parison effective to expand at least a portion of the parison effective that at least a portion of the parison contacts an inner surface of the chamber, thereby forming an inflatable member;

e) separating the first and second mold pieces to access the inflatable member within the first and third internal chambers, and removing the inflatable member from the variable-length chamber; and f) securing the inflatable member to an elongated catheter shaft, to form the balloon catheter.

8. The method of claim 6 wherein the second mold piece has an end with an external shoulder which is configured to fit into an internal shoulder of the first mold piece, and e) comprises separating the mold along the intersection of the external and internal shoulders to allow for removal of the inflatable member.

* * * * *

UNITED STATES PATENT AND TRADEMARK OFFICE
CERTIFICATE OF CORRECTION

PATENT NO. : 7,060,218 B2 Page 1 of 1
APPLICATION NO. : 10/990046
DATED : June 13, 2006
INVENTOR(S) : Johann J. Skinner et al.

It is certified that error appears in the above-identified patent and that said Letters Patent is hereby corrected as shown below:

Column 19,
Line 2, delete "m old" and insert --mold--.

Signed and Sealed this

Seventh Day of November, 2006

JON W. DUDAS
*Director of the United States Patent and Trademark Office*